(12) United States Patent
Kaufman et al.

(10) Patent No.: US 6,207,159 B1
(45) Date of Patent: Mar. 27, 2001

(54) METHODS FOR THE DIAGNOSIS AND TREATMENT OF INSULIN-DEPENDENT DIABETES MELLITUS

(75) Inventors: Daniel L. Kaufman, Santa Monica; Jide Tian, Los Angeles, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/119,922

(22) Filed: Jul. 21, 1998

Related U.S. Application Data

(60) Division of application No. 08/890,152, filed on Jul. 9, 1997, now Pat. No. 6,022,697, which is a continuation-in-part of application No. 08/758,414, filed on Nov. 29, 1996, now abandoned.

(51) Int. Cl.⁷ .................... A61K 39/00; A61K 45/00; A61K 38/28; A61K 38/43; A01N 63/00

(52) U.S. Cl. .................... 424/184.1; 424/278.1; 424/283.1; 424/93.7; 424/520; 424/556; 424/572; 424/810; 514/2; 514/3; 514/4; 514/21; 514/866; 530/351; 530/403

(58) Field of Search ............ 424/184.1, 278.1, 424/283.1, 93.7, 520, 556, 572, 810; 514/2, 3, 4, 21, 866; 530/403, 351

(56) References Cited

U.S. PATENT DOCUMENTS 5,762,937 * 6/1998 Atkinson et al. ............ 424/198.1

FOREIGN PATENT DOCUMENTS

| | | |
|---|---|---|
| 95/27500 | 10/1995 | (WO) . |
| 96/06630 | 3/1996 | (WO) . |
| 96/39176 | 12/1996 | (WO) . |
| 97/02016 | 1/1997 | (WO) . |
| 97/02052 | 1/1997 | (WO) . |

OTHER PUBLICATIONS

Rocken et al., *Immunology Today* 17(5):225–231 (1996).
Mosmann et al., *Immunology Today* 17(3):138–146 (1996).
Tisch et al., *Nature* 366:72–75 (1993).
Kaufman et al., *Nature* 366:69–72 (1993).
Petersen, JS et al. Autoimmunity. 25(3):129–138, Jun. 1997.*
Bieg, S et al. Diabetologia. 40(7):786–792, Jul. 1997.*
Chen, N et al. Transplantation. 60(11):1187–1193, Dec. 1995.*
Strom, TB et al. Curr. Opin. Immunol. 8(5):688–693, Oct. 1996.*
Nickerson, P et al. Curr. Opin. Immunol. 6(5):757–764, Oct. 1994.*
Tian, J et al. J. Exp. Med. 183:1561–1567, Apr. 1996.*

* cited by examiner

*Primary Examiner*—Christina Chan
*Assistant Examiner*—F. Pierre VanderVegt
(74) *Attorney, Agent, or Firm*—Flehr Hohbach Test Albritton & Herbert LLP; Todd A. Lorenz

(57) ABSTRACT

Methods for detecting the status of an insulin-dependent diabetes mellitus (IDDM)-associated autoimmune response in a mammal are provided. Specifically, the ratio of the frequency of T helper 1 cells to T helper 2 cells specific for a pancreatic β-cell associated antigen is indicative of the status of the autoimmune response. The methods may be employed prior to the onset of the clinical symptoms of the disease, thereby allowing identification of those at risk for developing clinical symptoms of IDDM, or subsequent to pancreatic tissue transplantation, for example, to measure the efficacy of treatment directed to enhancing the lifetime of the tissue transplant. Methods for prolonging the survival of tissue transplants are also provided. Specifically, a tissue-associated antigen is administered to the mammal which serves to shift the pathogenic Th1 response associated with pathological immunity toward a protective Th2 response.

18 Claims, 5 Drawing Sheets

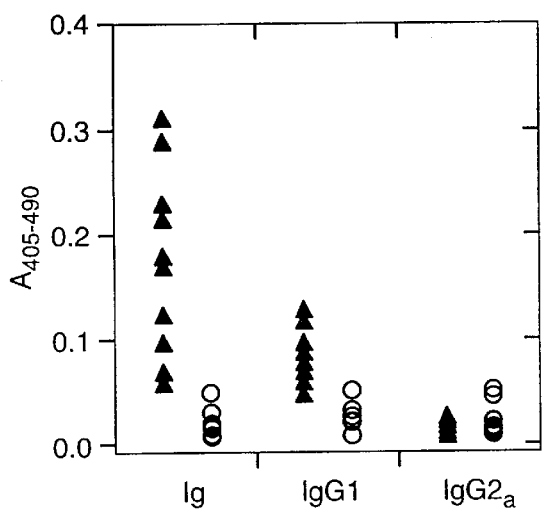
FIG._1A
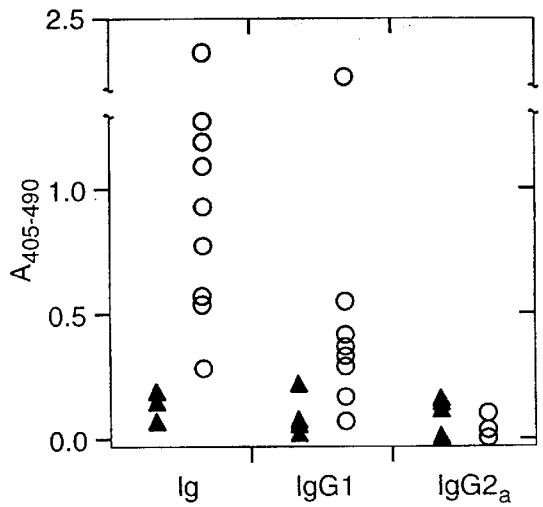
FIG._1B
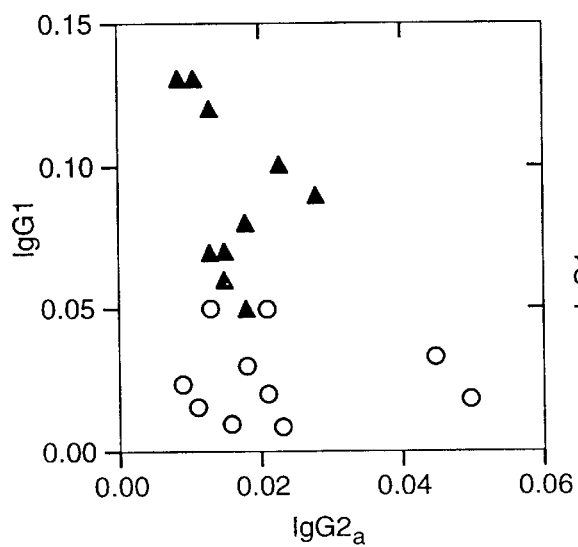
FIG._1C
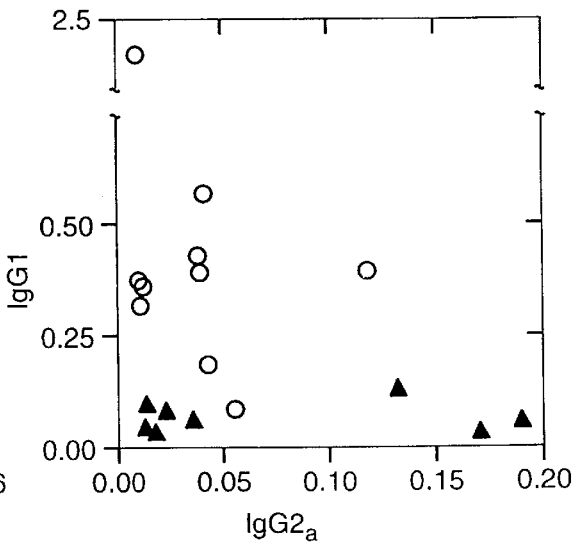
FIG._1D

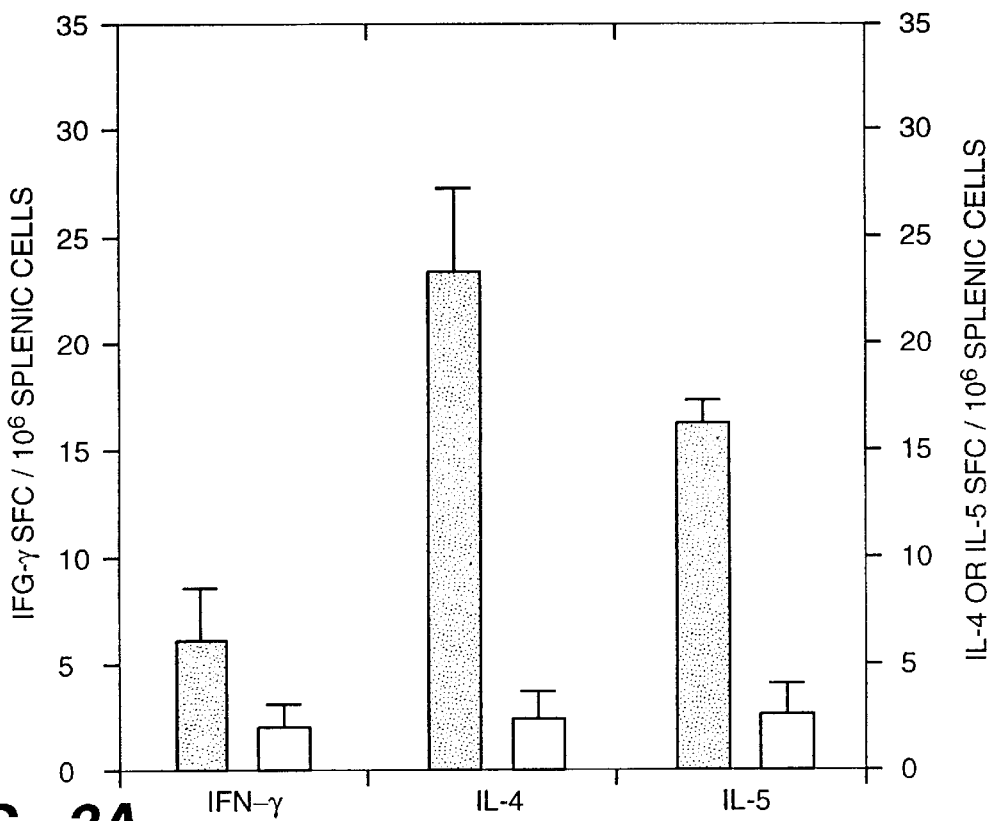
FIG._2A
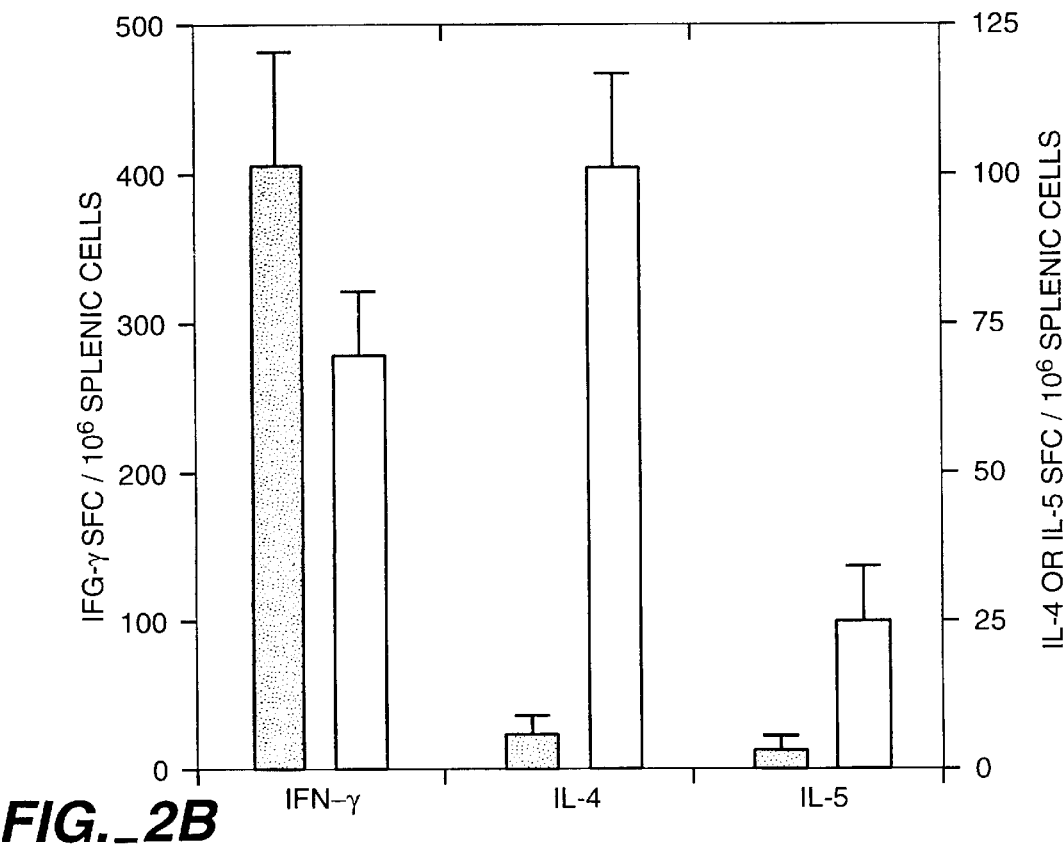
FIG._2B

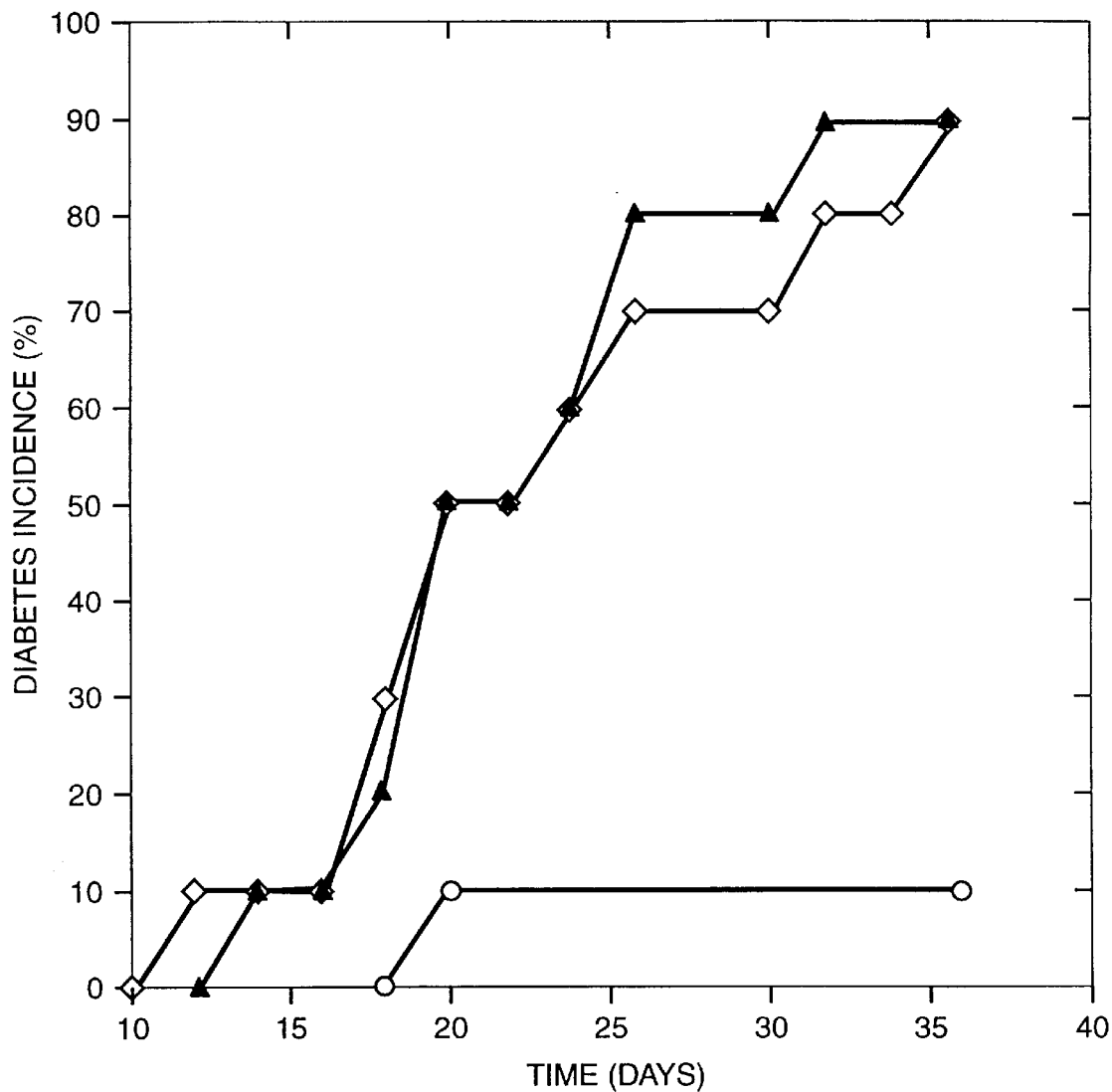
FIG._3

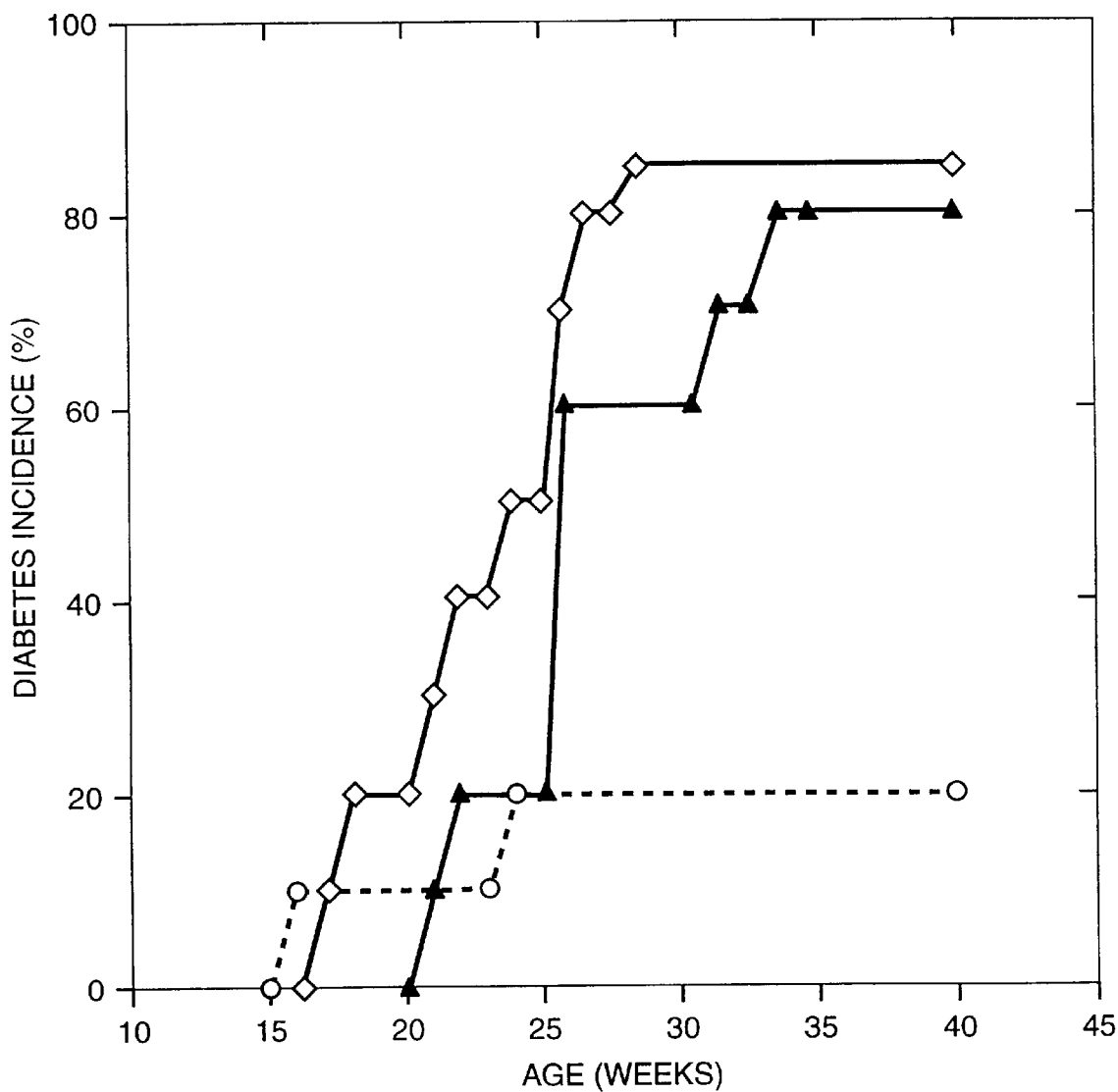
FIG._4

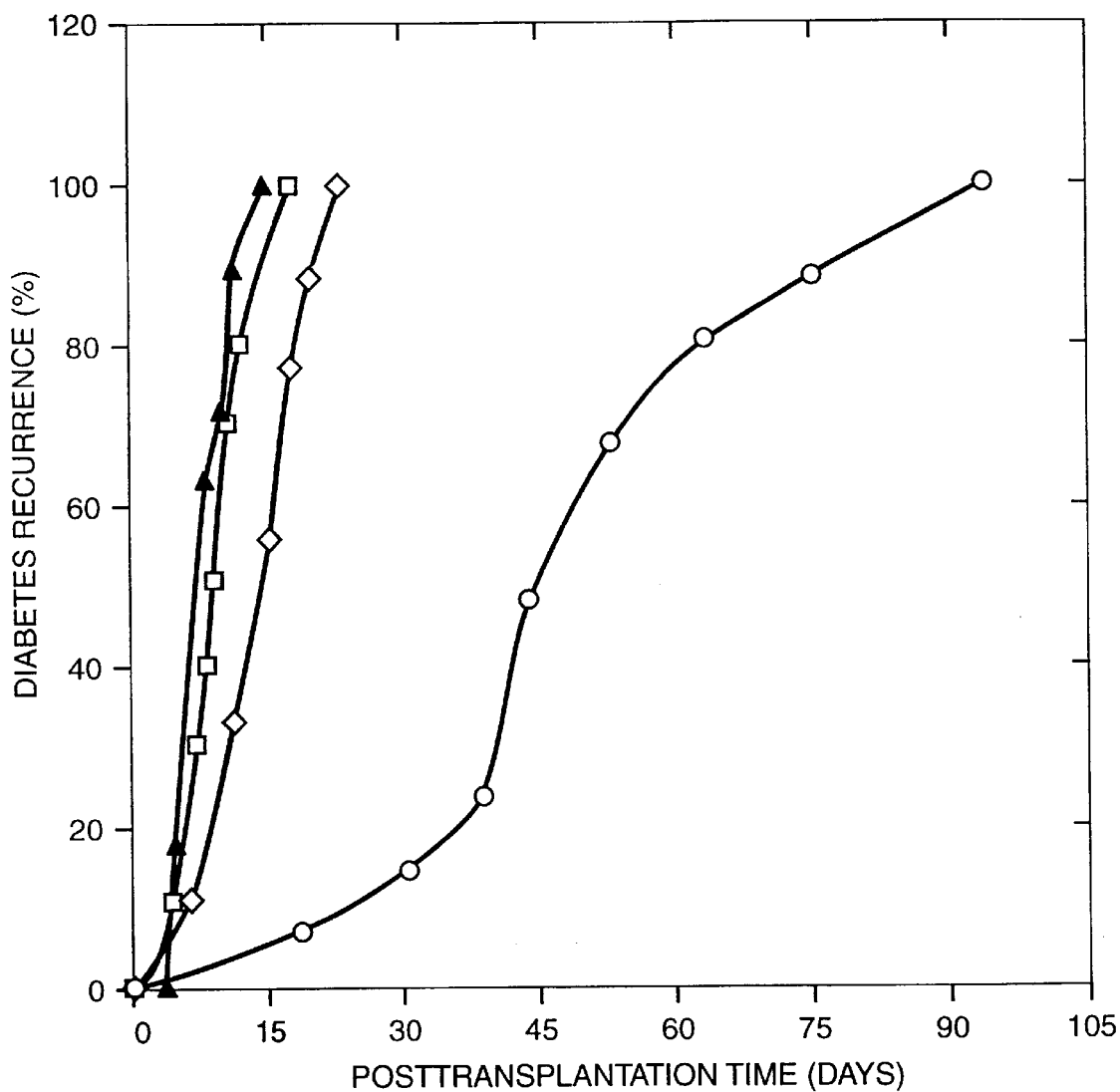
FIG._5

METHODS FOR THE DIAGNOSIS AND TREATMENT OF INSULIN-DEPENDENT DIABETES MELLITUS

This is a division of application U.S. Ser. No. 08/890,152 filed Jul. 9, 1997, now U.S. Pat. No. 6,022,697, which is a continuation-in-part of application Ser. No. 08/758,414 filed Nov. 29, 1996, abandoned.

This invention was made with Government support under Grant No. DK48455, awarded by the National Institutes of Health. The Government has certain rights in this invention.

FIELD OF THE INVENTION

The present invention relates to improved methods for diagnosing and treating insulin-dependent diabetes mellitus in mammals.

BACKGROUND

Insulin-dependent diabetes mellitus (IDDM; type I diabetes) is one of the most commonly occurring metabolic disorders in the world. In the United States, IDDM affects approximately one in 300 to 400 people, and epidemiological studies suggest that its incidence is continuing to increase. IDDM is caused by an autoimmune response that results in the T lymphocyte-mediated destruction of the insulin-producing β-cells of the pancreas. Castrano et al., *Ann. Rev. Immunol.* 8:647–679 (1990). Unfortunately, however, although the general mechanism by which IDDM occurs is known, IDDM becomes clinically evident only after the vast majority (approximately 80% or more) of the pancreatic β-cells have been irrevocably destroyed and the individual becomes dependent upon an exogenous source of insulin. In other words, at the time that the disease becomes clinically evident, the autoimmune response is well established and has already caused irreparable damage to the insulin-producing pancreatic tissue.

Because autoimmune-induced pancreatic damage is far progressed by the time that clinical symptoms of IDDM become evident, successful treatment of the autoimmune response ideally should be initiated well before the patient begins to exhibit overt symptoms of diabetes and requires insulin replacement for his or her own lost capability to produce insulin. In fact, any form of therapy would be expected to be more effective if persons at risk could be identified before the onset of clinical symptoms and the concomitant destruction of pancreatic β-cells. Moreover, techniques useful for tracking progression of the IDDM-associated autoimmune response in patients would allow one to assess the effectiveness of therapies which could be employed after the onset of disease. There is, therefore, a need for quick and reliable techniques for diagnostically identifying persons at risk for developing the clinical symptoms of IDDM and for monitoring the progression of the autoimmune response in those persons.

Prior to the onset of clinical symptoms of IDDM but after the onset of the IDDM-associated autoimmune response, attempts have been made to control the established diverse autoreactive T cell population, thereby effectively inhibiting progression of the disease. For example, immunosuppressants and antibodies which are specifically directed against autoimmune T cells may be useful for delaying the onset of disease. However, such treatments lack specificity and often significantly debilitate immune system function. Moreover, immunotherapeutics directed at blocking T cell-receptor/major histocompatibility complex (MHC) interactions can be highly specific, but may also be confounded by the complexity of the autoreactive T cell population and the genetic diversity of MHCs within the patient population.

Once the clinical symptoms of IDDM become evident, numerous different therapies have been employed for treating the debilitating effects of the disease. For example, by far the most commonly employed therapy for the clinical symptoms of IDDM is exogenous insulin replacement. However, while insulin replacement therapy allows most IDDM patients to lead somewhat normal lives, insulin replacement is also imperfect and does not completely restore metabolic homeostasis. As a result, severe complications including dysfunctions of the eye, kidney, heart, and other organs are common in diabetic patients undergoing insulin replacement therapy.

Another common treatment for the clinical symptoms of IDDM is pancreatic or β-islet cell transplantation. However, the insulin-producing β-cells of transplanted tissues are often rapidly destroyed by the same autoimmune response which had previously destroyed the patient's own pancreatic tissue. Therefore, the use of immunosuppressants after transplantation is common, carrying with it the adverse side effects described above.

As such, in addition to the urgent need for improved methods for the early diagnostic identification of persons who are at risk for developing the clinical symptoms of IDDM and for monitoring the progression of the autoimmune response in those at risk persons, there is also an urgent need for improved methods for therapeutically treating those persons who already exhibit clinical symptoms of the disease. Specifically, there exists a need for methods effective in prolonging the lifetime of tissue transplants, for example pancreatic tissue transplants, in mammals without the use of immunosuppressants and for inhibiting the T cell-mediated autoimmune mechanism underlying the disease.

The autoimmune response underlying IDDM is thought to be mediated by proinflammatory T helper 1(Th1) cells; cells that are known to secrete interferon-γ(IFN-γ) and promote the production of murine IgG2a isotype antibodies that are directed against pancreatic β-cell-associated autoantigens. In contrast to Th1 cells, T helper 2(Th2) cells are known to secrete interleukin-4 (IL-4) and interleukin-5 (IL-5) and promote the production of murine IgG1 isotype antibodies directed against pancreatic β-cell-associated autoantigens. We have herein tested whether at advanced stages of the IDDM-associated autoimmune response, the diverse Th1 cell pool could be downregulated by the induction of an anti-inflammatory Th2response to a single β-cell-associated antigen, thereby effectively reducing the autoimnmune-mediated destruction of the pancreatic tissue.

We have previously shown in an animal model of human IDDM, the nonobese diabetic (NOD) mouse, that a pathogenic Th1 response to the β-cell-associated autoantigen glutamic acid decarboxylase (GAD) arises at 4 weeks of age, concurrent with the onset of insulitis in these animals. Kaufman et al., *Nature* 366:69–72 (1993). GAD is a mammalian protein which serves to catalyze the rate-limiting step in the synthesis of γ-aminobutyric acid (GABA), a major inhibitory neurotransmitter of the mammalian central nervous system. Spink et al., *J. Neurochem.* 40:1113–1119 (1983), Huang et al., *Proc. Natl. Acad. Sci. U.S.A.* 87:8491–8495 (1990), Kobayashi et al., *Neurosci.* 7:2768–2772 (1987), Chang et al.,*J. Neurosci.* 8:2123–2130 (1988), Bu et al.,*Proc. Natl. Acad. Sci. U.S.A.* 89:2115–2119 (1992), Karlsen et al., *Diabetes* 41:1355–1359 (1992) and U.S. Pat. No. 5,475,086, issued Dec. 12, 1995. The GAD protein is present on various tissues and exists in multiple isoforms, one of which is GAD65, an antigen found to be associated with pancreatic β-cells. Subsequent to the anti-GAD Th1 response described above, T-cell autoimmunity appears to spread to other β-cell antigens such as a 65 kD heat shock protein (hsp65), insulin B-chain, carboxypeptidase H and peripherin in a cascade of autoimmune responses that ultimately leads to IDDM. Kaufman et al., supra and Tisch et al., Nature 366:72–75 (1993).

Thus, methods for shifting a pathogenic Th1-associated autoimmune response to a protective anti-inflammatory Th2 response would be useful for inhibiting the destructive effects of the autoimmune response and, therefore, for inhibiting and/or delaying the onset of clinical symptoms of IDDM and for prolonging the survival of pancreatic tissue transplants. Moreover, an analysis of the Th1/Th2 profiles of any particular subject will provide information as to risk for developing the clinical symptoms of IDDM and for determining progression of the autoinmmune response and the effect of therapies after the onset of the autoimmune response.

SUMMARY OF THE INVENTION

It is an object of the present invention to provide methods for detecting the status of insulin-dependent diabetes mellitus (IDDM)-associated autoimmunity in a mammal who is at risk of developing the clinical symptoms of IDDM or who has undergone a pancreatic tissue transplant. Accordingly, in one aspect, the present invention is directed to methods for detecting the status of IDDM-associated autoimmunity in a mammal which comprises determining the frequency of T helper 1 and T helper 2 cells in the subject which are specific for a pancreatic β-cell-associated antigen. IDDM-associated autoimmune destruction of insulin-producing pancreatic β-cells is a result of the presence of β-cell-associated antigen-specific T helper 1 cells; T cells which can be identified by their ability to secrete interferon-γ(IFN-γ). As demonstrated herein, however, induction of a Th2 response, thereby resulting in a relative increase in the number of T helper 2 cells as compared to T helper 1 cells specific for the β-cell-associated antigen, is indicative of protection against further destruction of pancreatic β-cells. In contrast to T helper 1 cells, the presence of T helper 2 cells can be detected by their ability to secrete interleukin-4 (IL-4) and interleukin-5 (IL-5). Preferably, the β-cell-associated antigens are autoantigens. Illustrative β-cell-associated autoantigens include GAD65, hsp65 and insulin B-chain. This diagnostic method can be employed prior to the onset of clinical symptoms, for the purposes of detecting the status of the IDDM-associated autoimmune response and determining whether the subject is at risk for developing IDDM, or subsequent to the onset of clinical symptoms, for the purposes of detecting the status of the autoimmune response against a pancreatic tissue transplant.

In another aspect, the status of IDDM-associated autoimmunity in a mammal who is at risk of developing the clinical symptoms of IDDM or who has undergone a pancreatic tissue transplant can be detected by determining the isotype of antibodies present in the subject which are directed against a specific β-cell-associated antigen. As demonstrated herein, the presence of pathogenic T helper 1 cells specific for a β-cell-associated antigen in mice induces the production of IgG2a isotype antibodies against that antigen whereas the presence of protective T helper 2 cells specific for the antigen induces the production of IgG1 isotype antibodies against that antigen. As such, by measuring the relative numbers of IgG2a and IgG1 isotype antibodies against a specific β-cell-associated antigen (or the corresponding isotype antibodies from other mammals which are indicative of the presence in the mammal of T helper 1 and T helper 2 cells directed against the β-cell-associated antigen), one may determine the status of the autoimmune response in the subject.

It is a further object of the present invention to provide an improved method for prolonging the survival of a tissue transplant in a mammal. Specifically, the present invention is directed to a method for prolonging the survival of a tissue transplant in a mammal by administering to that mammal a tissue transplant protecting amount of an antigen which is associated with the donor transplanted tissue. As demonstrated herein, the administration of a pancreatic β-cell-associated antigen to a mammal either prior to or shortly after pancreatic tissue transplantation results in an increased ratio of the number of protective T helper 2 cells specific for that antigen to the number of pathogenic T helper 1 cells specific for that antigen. As such, this shift from a pathogenic Th1 response toward a protective Th2 response results in inhibition of the immune response and an effective increase in the lifetime of the tissue transplant. The method may be practiced with antigens derived from virtually any tissue which is transplanted and which results in the induction of a T cell-mediated immune response.

A further object of the present invention is to provide a method for reducing the severity of an IDDM-associated autoimmune response in a mammal comprising administering to the mammal a therapeutically effective amount of a pancreatic β-cell-associated antigen, wherein the administration of the antigen results in an increase in the ratio of the number of T helper 2 cells specific for that antigen to the number of T helper 1 cells specific for that antigen. The antigen may be administered alone or in combination with an adjuvant for the purpose of increasing the T helper 2/T helper 1 ratio.

Another embodiment of the present invention is directed to a method for increasing the frequency of T helper 2 cells specific for a tissue-associated antigen relative to T helper 1 cells specific for the tissue-associated antigen which comprises administering to the mammal the tissue-associated antigen in an amount sufficient to induce a T helper 2 cell response to the antigen.

These and other aspects of the invention will become evident upon reference to the following detailed description and the attached drawings.

BRIEF DESCRIPTION OF THE DRAWINGS

FIGS. 1A–1D show that antigen administration to non-obese diabetic (NOD) mice induces antigen-specific IgG1 antibodies. Specifically, animals were treated with β-galactosidase (▲) or glutamic acid decarboxylase 65 (GAD65) (○) and antibodies to β-galactosidase (FIGS. 1A and 1C) and GAD65 (FIGS. 1B and 1D) were characterized using isotype-specific ELISA assays. The data are represented as the mean absorbance values over background of triplicate samples from individual mice (n=10 for each group). The background absorbance ranged between 0.06 and 0.1. Experimental and control serum samples were tested simultaneously in two separate assays. In FIGS. 1C and 1D, data is presented as the levels of IgG1 versus the levels of IgG2a in individual mice.

FIGS. 2A–2B show that antigen administration to NOD mice stimulates the expansion of antigen-specific Th2 cells. Specifically, the frequency of β-galactosidase-specific (FIG.

2A) and GAD65-specific (FIG. 2B) interferon-γ-(IFN-γ), interleukin-4- (IL-4) and interleukin-5- (IL-5) secreting splenic T cells in β-galactosidase- (■) and GAD65- (□) treated mice were determined by ELISPOT. Data are represented as the mean number of spot-forming colonies (SFC) per $10^6$ splenic T cells ± s.e.m. Samples were tested in triplicate. Experimental and control mice were tested simultaneously in two separate experiments (n=5 for each group).

FIG. 3 shows that adoptive cotransfer of splenic T cells from GAD65-treated mice protects recipient mice from IDDM. Specifically, splenic mononuclear cells from mice treated with β-galactosidase (▲) or GAD65 (○) were cotransferred with T cells from diabetic NOD mice to 5-week-old irradiated female NOD mice. A positive control group received cells only from untreated-diabetic NOD mice (◇). Blood glucose levels were monitored frequently, and animals were considered diabetic after two consecutive blood glucose levels of >13 mmol/1 (n=10 for all groups).

FIG. 4 shows that administration of GAD65 after the establishment of β-cell autoinmnunity inhibits disease progression. Specifically, female NOD mice were treated at 8 weeks of age with IFA alone (◇), β-galactosidase (▲) or GAD65 (○). The mice were followed for the onset of hyperglycemia (n=10 for each group).

FIG. 5 shows that administration of GAD65 prolongs survival of syngeneic islet grafts in diabetic NOD mice. Islets were transplanted into diabetic NOD mice that had been treated with β-galactosidase (▲), GAD65 (○), insulin B-chain (□), or hsp65 peptide (◇), and insulin administration was discontinued. Data are presented as time post transplantation at which hyperglycemia recurred (blood glucose levels >13 mmol/1). (n=14 for β-galactosidase, n=17 for GAD65, n=9 for insulin B chain and n=11 for hsp65).

DESCRIPTION OF THE SPECIFIC EMBODIMENTS

The present invention is based at least in part upon the surprising finding that a shift from a T helper 1 (Th1) response towards a T helper 2 (Th2) response specific for a pancreatic β-cell-associated antigen results in protection against the pancreatic β-cell destruction that is associated with IDDM-associated autoimmunity. As such, the correlation between a shift from a Th1 response to a Th2 response and protection against the autoimmune-induced destruction of pancreatic β-cells can be exploited for both diagnostic and therapeutic purposes.

Accordingly, in one embodiment, the present invention is directed to a method for detecting the status of an IDDM-associated autoimmune response in a mammal. The term "detecting the status" when used in reference to IDDM-associated autoimmunity means determining the degree to which the autoimmune response has progressed in the subject or, in the case where the method is performed subsequent to a pancreatic tissue transplant, to determine if a therapy is working to enhance the lifetime of the tissue transplant by lessening the pathogenic anti-β-cell autoimmune response. It is well known that the autoimmune mechanism underlying IDDM is far progressed by the time that clinical symptoms of the disease become evident and, therefore, one may determine the degree to which the autoimmune response has progressed in a subject even before the onset of clinical symptoms of the disease.

A mammalian subject is "diagnosed as having" IDDM once clinical symptoms of the disease become evident. For the most part, this occurs at the time that the subject requires an exogenous source of insulin to survive. Detecting the status of an IDDM-associated autoimmune response in subjects who have been diagnosed as being at risk for IDDM is useful, for example, for monitoring or measuring the efficacy of a treatment to inhibit disease progression. Prior to the onset of clinical symptoms of the disease, a subject may also be "at risk of having" IDDM. This term is intended to define those persons who have not yet developed clinical symptoms of IDDM but who exhibit IDDM-associated autoimmunity. As such, one may detect the status of an IDDM-associated autoimmune response in a subject prior to onset of the clinical symptoms of the disease.

One may detect the status of an IDDM-associated autoimmune response in a subject in a number of ways. For example, as demonstrated herein, because the characteristics and clinical symptoms of the disease are associated with the presence of T helper 1 cells specific for various pancreatic β-cell-associated antigens, and because a shift from a pathogenic Th1 response toward a Th2 response, thereby resulting in an increase in the ratio of the number of T helper 2 cells for a specific pancreatic β-cell-associated antigen to the number of T helper 1 cells specific for that antigen, is indicative of a protective effect and a lessening of the severity of the destructive IDDM-associated autoimmune response, determining the frequency of T helper 1 and T helper 2 cells in the subject that are specific for a pancreatic β-cell-associated antigen is indicative of the status of the autoimmune response. For example, an increase in the ratio of T helper 1 cells as compared to T helper 2 cells specific for a particular pancreatic β-cell-associated antigen is indicative of a worsening of the destructive autoimmune response, whereas a decrease in that ratio is indicative of a reduction in the severity of the destructive autoimmune response. As such, the ratio of T helper 1 cells specific for a pancreatic β-cell-associated antigen to T helper 2 cells specific for that antigen is indicative of the status of the autoimmune response.

The frequency or number of T helper 1 and T helper 2 cells specific for a pancreatic β-cell-associated antigen that are present in the subject may be determined using techniques that are available and well known in the art. For example, T helper 1 cells are known to secrete IFN-γ whereas T helper 2 cells are known to secrete IL-4 and IL-5. One may determine the frequency of IFN-γ-, IL-4- and IL-5-secreting T cells that are specific for a particular pancreatic β-cell-associated antigen by employing the ELISPOT assay described by Forsthuber et al., *Science* 271:1728–1730 (1996), by cytokine quantitation by ELISA or by quantitative PCR analysis of the mRNAs encoding the cytokines. Other T helper 1 and/or T helper 2 cell specific markers may also find use as predictive markers of the presence of these cells.

One may also detect the status of an IDDM-associated autoimmune response in a subject by determining the isotype of antibodies present in the subject that are specifically directed against a pancreatic β-cell-associated antigen. For example, as demonstrated herein, the presence of specific antibody isotypes are associated with the presence of pathogenic T helper 1 cells and protective T helper 2 cells, wherein the isotypes specific for each cell type differ. Specifically, murine IgG2a isotype antibodies are associated with the presence of T helper 1 cells and murine IgG1 antibodies (corresponding to IgE and IgG4 antibodies in humans) are associated with the presence of T helper 2 cells. As such, the ratio of the number of T helper 2 cell-associated isotype antibodies to the number of T helper 1 cell-associated isotype antibodies which are specifically directed against a pancreatic β-cell-associated antigen is indicative of the status of the autoimmune response. With regard to antibodies, use of the term "specifically directed against" means that the antibody is capable of binding to an epitope present on the pancreatic β-cell-associated antigen. Methods for determining specific binding of antibodies to antigenic epitopes and for determining the isotype of antibodies are well known in the art.

The terms "pancreatic β-cell-associated antigen", "β-cell-associated antigen" and grammatical equivalents thereof are intended to denote the various antigenic determininants present on pancreatic β-cells to which autoimmune responses may be directed, thereby resulting in the destruction of insulin-producing pancreatic β-cells. Exemplary antigens present on mammalian pancreatic β-cells to which autoimmune responses may be directed include GAD65 (see U.S. Pat. No. 5,475,086), heat shock protein 65 (hsp65; see U.S. Pat. No. 5,114,844), insulin, insulin B-chain, carboxypeptidase H and peripherin. Other pancreatic β-cell-associated antigens are known in the art. The identification of T helper 1 and T helper 2 cells specific for these antigens and/or antibody isotypes specifically directed against these antigens may be performed as described above.

In another embodiment, the present invention is directed to a method for prolonging the survival of a tissue transplant in a mammal wherein the method comprises the step of administering to the mammal a tissue transplant protecting amount of an antigen which is associated with the donor tissue. Antigens which are "associated with the donor tissue" are those antigens which represent the MHC characteristics of the donor tissue The term "prolonging the survival of" when used in regard to tissue transplants means that a tissue transplant in the presence of the administration of a tissue transplant protecting amount of a tissue-associated antigen is maintained in an functional state for a longer period of time than is a tissue transplant in the absence of any associated antigen administration. By "functional state" is meant that the transplanted tissue retains it normal physiological function.

A "pancreatic tissue transplant" may comprise an entire pancreas, with or without associated structures, or may comprise only a portion of an entire pancreas capable of producing insulin. Pancreatic β-islet cells are an example of the latter type of transplant.

Administration of a tissue transplant protecting amount of a donor tissue-associated antigen results in an increase in the ratio of the number of protective T helper 2 cells to pathogenic T helper 1 cells specific for that antigen, thereby effectively reducing the pathogenic immune destruction of cells of the transplanted tissue and, in turn, resulting in an effective increase in the lifetime of the tissue transplant. In some cases, there will have been no initial pathogenic T helper 1 cell response to the antigen of interest so a mere increase in the number of protective T helper 2 cells serves to increase the T helper 2/T helper 1 ratio. By "tissue transplant protecting amount" is meant the amount of donor tissue-associated antigen sufficient to increase the ratio of Th2 to Th1 cells specific for that antigen, thereby reducing the destructive autoimmune response and effectively prolonging the lifetime of the tissue transplant in the host. This amount should not be so high so as to cause adverse side effects, such as unwanted cross reactions, anaphylactic reactions, and the like and will differ depending upon the nature of the host, the nature of the transplanted tissue, the clinical setting, the severity and degree of the disease, the mode of administration, and the like. The amount of donor tissue-associated antigen administered can be determined empirically by those of ordinary skill in the art and without undue experimentation and can be adjusted by the individual physician in the event of any counterindications. A tissue transplant protecting amount may vary from about 0.1 mg/m$^2$ to about 2000 mg/m$^2$, preferably from about 0.1 mg/m$^2$ to 500 mg/m$^2$/dose, in one or more dose administrations daily, for one or several days or boosted in regular intervals (for example, once every two to six months).

Pancreatic β-cell-associated antigens which find use for administration to mammalian subjects include the various antigenic molecules present on pancreatic β-cells to which immune responses may be directed. Exemplary antigens present on mammalian pancreatic β-cells which are useful for administration include GAD65 (see U.S. Pat. No. 5,475,086), heat shock protein 65 (hsp65; see U.S. Pat. No. 5,114,844), insulin, insulin B-chain, carboxypeptidase H, peripherin, and other pancreatic β-cell-associated antigens and autoantigens which are known in the art. Either the natural, intact antigen may be administered, either unconjugated or conjugated to other molecules such as radionuclides, and the like, or "conservative amino acid variants" of the antigen may be employed; the phrase "pancreatic β-cell-associated antigen" being intended to encompass such variants. Antigens derived from other non-β-cell pancreatic tissue may also find use herein.

Conservative amino acid variants of tissue-associated antigens, including pancreatic β-cell-associated antigens and autoantigens, may be produced and screened for functionality by techniques which are routine in the art. Conservative amino acid variants are variant antigens which possess at least one conservative amino acid substitution in its amino acid sequence, the substitution(s) not substantially affecting the ability of the molecule to prolong the survival of a tissue transplant or to shift a Th1 response toward a Th2 response. Conservative amino acid substitutions preferably are made in accordance with the following Table 1 when it is desired to modulate finely the characteristics of a tissue-associated antigen (amino acids presented in their standard three letter amino acid codes).

TABLE 1

| Original Residue | Exemplary Substitutions |
| --- | --- |
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Tissue-associated antigens, including pancreatic β-cell-associated antigens, which find use may also be "deletional" or "insertional" variants of the natural molecule which are variants possessing deletions or insertions, respectively, from the natural amino acid sequence. Such variants retain a substantial amino acid sequence homology to the natural antigen and retain the functional ability to prolong the survival of a tissue transplant or by shifting a Th1 response toward a Th2 response. By "substantial amino acid sequence homology" is meant that the variant retains an amino acid homology greater than 70%, preferably at least about 80%, and more preferably at least about 90% with the natural polypeptide sequence. Techniques for producing and screening such variants for functionality are well known in the art and could be routinely employed without undue experimentation.

The tissue-associated antigen of interest can be administered parenterally by injection, inhalationally, orally or by gradual perfusion over time. The pancreatic β-cell-associated antigen can be administered intravenously, intraperitoneally, intramuscularly, subcutaneously, intracavity, transdermally, intranasally, or enterally. The antigen of choice may be administered either prior to or after the donor tissue is transplanted in the host, preferably immediately before or immediately after transplantation, with the only caveat being that the administration be performed at a time which allows for the autoimmune-induced destruction of the transplanted tissue to be reduced.

Preparations for parental administration include sterile aqueous or non-aqueous solutions, suspensions, aerosols and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solutions, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases, and the like.

In yet another embodiment, the present invention is directed to a method for reducing the severity of an IDDM-associated autoimmune response in a mammal comprising administering to the mammal a therapeutically effective amount of a pancreatic β-cell-associated antigen, wherein administration of the antigen results in an increase in the ratio of the number of T helper 2 cells specific for the antigen to the number of T helper 1 cells specific for the antigen. The term "ameliorate" or "ameliorating" denotes a lessening of the detrimental effect or severity of the autoimmune response in the subject receiving therapy, the severity of the response being determined by means which are well known in the art. The term "therapeutically effective amount" means that the amount of pancreatic β-cell-associated antigen used for administration is sufficient to reduce the severity of the autoimmune response. Therapeutically effective amounts will differ based upon the nature of the patient, the degree and severity of the autoimmune response, the clinical setting, the mode of administration, and the like and can be determined empirically by the skilled practitioner without undue experimentation. A therapeutically effective amount may vary from about 0.1 mg/kg to about 2000 mg/kg, preferably from about 0.1 mg/kg/dose to about 500 mg/kg/dose, in one or more dose administrations daily, for one or several days or boosted in regular intervals.

The "clinical symptoms" of IDDM are well known to those skilled in the art and include, for example, the requirement that the subject be placed on an exogenous source of insulin for survival.

For administration purposes, a tissue-associated antigen may be administered alone or in conjunction with an adjuvant which useful for inducing a T helper 2 response. By "T helper 2 response" is meant a shift in the Th1-based autoimmune response toward a Th2-based response, wherein the number of T helper 2 cells specific for the antigen increases relative to the number of T helper 1 cells specific for the antigen, thereby reducing the severity of the immune response. A wide variety of adjuvants find use herein and include incomplete Freund's adjuvant (IFA), aluminum hydroxide, the RIBI adjuvant, GMDP, peptides derived from Leshmania, BCG and other peptides that preferentially induce Th2 responses, nucleic acids, including for example, immunogenic mRNA (imRNA) and DNA, cytokines, including for example, IL-4, interleukin-10 (IL-10), molecules such as B7-2 and IL-12 p40 dimer, and the like. Other adjuvants are known in the art and could be routinely employed by those skilled in the art to determine if they assist in the generation of a Th2 response.

T helper 2 responses may also be induced independent of the use of adjuvant by adjusting the dose of antigen administered, wherein higher doses and lower doses at frequent intervals favor the induction of a T helper 2 response relative to a T helper 1 response, and varying the site of administration, wherein sites such as the lung mucosa favor T helper 2 responses independent of adjuvant.

The following examples are offered by way of illustration, and not by way of limitation.

EXPERIMENTAL

Methods and Materials

Mice: NOD mice were purchased from Taconic Farms (Germantown, N.Y.) and bred under specific pathogen-free conditions. Only female NOD mice were used in this study. In our NOD mouse colony, insulitis begins at 4 weeks of age. The average age of disease onset is at 22 weeks, with about 80% of the mice displaying IDDM by 30 weeks of age.

Antigens: Mouse GAD65 (Lee et al., *Biochem. Biopphys. Acta* 1216:157–160 (1993)) and control *Escherichia coli* β-galactosidase were purified as previously described. Kaufman et al., supra. The hsp65 immunodominant peptide (Elias et al., *Lancet* 343:704–706 (1994)) was synthesized by standard fluorenyl methyloxycarbonyl (fmoc) chemistry and purified by chromatography. The amino acid composition of each peptide was verified by mass spectrometry. Insulin B-chain was purchased from Sigma.

GAD65 Autoantibody Assays: At 8 weeks of age, NOD mice received a single intraperitoneal (i.p.) injection of 100μg β-galactosidase or GAD65 in 50% IFA (Gibco BRL, Gaithersberg, Md.). Four weeks later, serum samples were tested for GAD65 and β-galactosidase antibodies by ELISA. β-Galactosidase or GAD65 (Synectics Biomedical, Stockholm) at 10 μg/ml was bound to 96-well plates (Nunc, Weisbaden, Germany), in 0.1 M NaHCO$_3$, pH 9.6 (β-galactosidase) or 8.5 (GAD65) at 4° C. overnight. the wells were rinsed with PBS and then blocked with 3% BSA in PBS for 1 hour. Mouse sera was added (0.1 ml of a 1/500 dilution) and incubated 1 hour at 37° C. Following washing, bound Ig was characterized using affinity-purified horseradish peroxidase (HRP)-coupled goat anti-mouse IgG+A+M (H+L), or HRP-coupled goat anti-mouse isotype specific antibodies for IgG1 and IgG2a (Southern Biotech Associates and ABTS). Serum samples from untreated BALB/c and AKR mice were used as negative controls.

ELISPOT Analysis: At 8 weeks of age, mice received a single i.p. injection of 100 μg β-galactosidase or GAD65 in 50% IFA. Fourteen days later, splenic T cells were isolated and the frequency of β-galactosidase and GAD65-specific T cells secreting IL-4, IL-5 and IFN-γ was determined by using the ELISPOT technique as previously described (Forsthuber et al., *Science* 271:1728–1730 (1996)), with the exception that GAD65 and β-galactosidase (100 μg/ml) were used as antigens, and 11B11 together with biotinylated BVD6-24G2 (PharMingen, San Diego, Calif.) was used for capture and detection of IL-4. The resulting spots were counted manually.

Adoptive Transfer of Diabetes: Eight-week-old NOD mice were injected i.p. with 100 μg GAD65 or control β-galactosidase in 100 μof 50% IFA and reinjected at 14 weeks of age. Five weeks later, single-cell suspensions of splenic mononuclear cells were prepared from each group, as well as from unmanipulated diabetic NOD mice. Ten million splenic mononuclear cells from the unmanipulated diabetic mice were mixed with an equal number of splenic mononuclear cells from GAD65 or β-galactosidase-treated mice and injected intravenously into 5-week-old female NOD mice that had received 500 rad γ-irradiation. Wicker et al., *Diabetes* 35:855–860 (1986). Another control group received $1 \times 10^7$ splenic mononuclear cells obtained only from unmanipulated, diabetic mice.

T-Cell Proliferation Assays: Female NOD mice were injected i.p. at 8 weeks of age with 100 μg GAD65, or control β-galactosidase, in 100 μl of 50% IFA. The mice were reinjected 2 weeks later. At 12 weeks of age, splenic T cells were tested for proliferative responses to GAD65, hsp65, β-galactosidase and the HEL peptide, as previously described. Kaufman et al., supra.

IDDM Incidence: At 8 weeks of age, groups of 10 female NOD mice were injected i.p. with 50 μl GAD65 or control β-galactosidase in 100 μl of 50% IFA. Another control group received 100μ of 50% IFA alone. Because there may be a requirement for continual antigen presentation (Ramsdell et al., *Science* 257:1130–1134 (1992)), the mice were reinjected every 6 weeks until 40 weeks of age. Urine glucose levels were monitored weekly for diabetes by Tes-tape (Lilly). After we observed abnormal glucose in the urine, blood glucose levels were monitored twice weekly. A recording of two consecutive blood glucose levels of >13 mmol/l was considered as IDDM onset.

Transplantation of Islets: Female NOD mice were monitored for the onset of IDDM, after which the mice were maintained on 1.0–1.5 units insulin (Humulin U, Lilly) per day. At the time of IDDM onset, mice were injected with either 100 μg of GAD65, hsp65, insulin B-chain or control β-galactosidase i.p. in 50% IFA. Ten days later the mice were reinjected. Ten days after the second treatment, 3000 freshly isolated islets from newborn NOD mice were transplanted into the space beneath the kidney capsule, and humulin administration was discontinued. The mice were reinjected every 2 weeks. Recurrence of diabetes is defined as two consecutive blood glucose levels of <13 mmol/l.

EXAMPLE 1

Antigen Administration Promotes a IgG1 Response

It was unknown whether it was possible to modulate GAD65-specific Th1/Th2 responses in prediabetic NOD mice and whether this could interfere with disease progression. As such, NOD mice were treated only once with GAD65 or control β-galactosidase in incomplete Freund's adjuvant (IFA) at 8 weeks of age, well after the onset of insulitis, as described in Materials and Methods. Four weeks after administration, serum collected from the animals was tested for the presence of antibodies directed against GAD65 or β-galactosidase by employing isotype specific ELISA assays. The results are presented in FIG. 1.

Specifically, the data presented in FIG. 1 demonstrate that anti-β-galactosidase immunoglobulins were readily detected in serum samples taken from the β-galactosidase-treated group, but were only slightly above the background levels in sera from the GAD65-treated group (FIG. 1A). The level of GAD65 antibodies in the β-galactosidase-treated group was similar to that found in untreated NOD mice (data not shown). Serial dilutions of sera showed a linear relationship with resulting absorbance measures. Antibodies to GAD65 in sera from untreated BALB/c and AKR mice were at background levels.

As also shown in FIG. 1, high levels of GAD65 autoantibodies were present in almost all serum samples from the GAD65-treated group, whereas mice injected with β-galactosidase had low levels of GAD65 autoantibodies (FIG. 1B), as did unmanipulated NOD mice (data not shown). The induced β-galactosidase and GAD65 antibodies were predominantly of an IgG1 isotype (FIG. 1), indicating these treatments primed antigen-specific Th2 help (as compared to IgG2a antibodies which correlate with a pathologic Th1 response). Mosmann et al., *Annu. Rev. Immunol.* 7:145–173 (1989). In individual mice, there tended to be an inverse correlation between IgG1 and IgG2a GAD65 antibody levels (FIG. 1D). Thus, a single administration of GAD65 to prediabetic NOD mice functioned to shift the pathogenic Th1 response toward a protective Th2 response as evidenced by the generation of Th2-dependent IgG1 GAD65 antibodies.

EXAMPLE 2

Antigen Administration Induces a Th2 Response

Traditionally, it has been difficult to define Th1 and Th2 activity because of the low precursor frequency of antigen-specific T cells. We used an improved ELISPOT assay (Forsthuber et al., *Science* 271:1728–1730 (1996)) to monitor frequency of splenic antigen-specific T cells that produce Th1-and Th2-type cytokines following the administration of control β-galactosidase or GAD65. We observed that β-galactosidase administration predominantly primed an increase in the frequency of interleukin-4 (IL-4) and interleukin-5 (IL-5) secreting β-galactosidase-specific Th2 cells (FIG. 2A). As expected, β-galactosidase-reactive T cells were infrequently observed in the GAD65-treated group.

Interferon-γ(IFNγ)-secreting GAD65-specific Th1 cells were frequently detected in β-galactosidase-treated mice whereas IL-4- and IL-5-secreting GAD65-specific Th2 cells were rarely detected (FIG. 2B). Following a single treatment with GAD65, however, there was a dramatic increase in the frequency of IL-4- and IL-5-secreting GAD65-reactive T cells (Th2 cells), which on average were 15- and 10-fold as frequent (respectively) as in the control group (FIG. 2B). Furthermore, the average frequency of GAD65-specific IFN-γ-secreting T cells (Th1 cells) in GAD65-treated mice was 65% of that found in the control group, suggesting that this treatment limited the expansion of Th1 responses to GAD65.

Therefore, ELISPOT analysis reveals that both β-galactosidase and GAD65 administration promoted the expansion of IL-4- and IL-5-secreting T cells (thereby confirming the activation of a specific Th2 response) and limited the expansion of IFN-γ secreting T-cells (thereby confirming the inhibition of the Th1 response). These data indicate that autoantigen administration induces a shift from a Th1 response to an antigen-specific Th2 response in recipient mice. Thus, even after the establishment of Th1 autoimmunity, it is possible to additionally engage Th2 cells and dramatically alter the balance of antigen-specific Th1/Th2 cells.

EXAMPLE 3

GAD65 Treatment Prevents Adoptive Transfer of IDDM

To examine whether the induced T-cell responses could inhibit an established pathogenic autoimmune response, we tested the ability of T cells from β-galactosidase- and GAD65-treated NOD mice to inhibit the adoptive transfer of diabetes. We observed that 90% of the mice receiving a mixture of splenic mononuclear cells from β-galactosidase-treated and diabetic mice developed IDDM within 5 weeks after transfer—similar to a positive control group that received mononuclear cells exclusively from diabetic mice (FIG. 3). However, only 10% of the mice that received a mixture of mononuclear cells from GAD65-treated and diabetic mice developed IDDM (P<0.01). Thus, consistent with the induction of an active tolerance mechanism, GAD65 (but not β-galactosidase) treatment induces potent regulatory cells in prediabetic NOD mice that are capable of blocking target tissue destruction by a diverse, activated effector T-cell population.

EXAMPLE 4

GAD65 Administration Inhibits Proliferative T-Cell Responses

We tested splenic-T-cells for proliferative responses to GAD65 and the immunodominant peptide of heat shock protein (hsp 65, peptide 277, see Elias et al., supra) 4 weeks after treatment. Splenic T cells from both mice treated with IFA (alone) and those treated with β-galactosidase displayed strong T-cell responses to GAD65 and hsp65 (Table 2), which were similar in magnitude to the responses by splenic T cells from age-matched unmanipulated NOD mice. Kaufman et al., supra. In contrast, NOD mice injected with GAD65 displayed markedly reduced proliferative T-cell responses to GAD65 (Table 2). As ELISPOT analysis revealed that the frequency of GAD65-reactive Th1 cells was reduced by only 32% in GAD65-treated mice (FIG. 2b), these data suggest that the primed GAD65-specific Th2 response actively downregulated Th1 proliferation in vitro. However, responses to control concanavalin A (con A) and recall responses to hen egg white lysozyme (HEL) were unaffected by GAD or β-galactosidase treatment (Table 2). It is interesting that the inhibitory effect was not confined only to the administered autoantigen, as proliferative responses to hsp65 were also reduced in GAD65-treated mice. Indeed, the frequency of hsp65-reactive Th1 cells, as determined by ELISPOT analysis, was reduced by 30% in GAD65-treated prediabetic NOD mice (data not shown), suggesting that the induction of GAD65-specific Th2 responses limited the inflammatory cascade of β-cell reactive T-cell responses.

Thus, GAD65 administration markedly reduces proliferative T-cell responses to not only GAD65, but to other β-cell autoantigens (such as hsp65), thereby effectively inhibiting the autoimmune cascade which results in destruction of pancreatic β-islet cells.

TABLE 2

GAD65 Administration Inhibits Proliferative T-Cell Responses to β-cell Autoantigens, Reduces Intraislet IFN-γ transcription and Insulitis.

| | Treatment | | |
|---|---|---|---|
| | IFA alone | β-galactosidase | GAD65 |
| A. Spleen Cells | | | |
| β-galactosidase | 1.1 ± 0.2 | 4.1 ± 1.9 | 1.3 ± 0.2 |
| GAD65 | 10.9 ± 2.6 | 13.1 ± 2.9 | 4.2 ± 0.9 |
| hsp65 | 10.9 ± 1.9 | 11.5 ± 3.4 | 7.3 ± 2.5 |
| HEL | 1.0 ± 0.2 | 1.1 ± 0.1 | 0.9 ± 0.3 |
| ConA | 18.6 ± 2.1 | 20.3 ± 1.4 | 18.1 ± 1.2 |
| B. Lymph Node Cells | | | |
| HEL | 47.8 ± 3.4 | 50.3 ± 2.9 | 48.7 ± 4.3 |
| PPD | 52.4 ± 4.7 | 50.1 ± 3.6 | 56.7 ± 3.1 |
| C. Insulitis Score | 2.6 ± 0.7 | 2.1 ± 1.6 | 1.3 ± 1.3 |

The mean antigen-induced T-cell proliferation over background was expressed as stimulation index ± s.e.m. (n = 6 for each group). Primed lymph node T-cell recall responses to HEL or purified protein derivative (PPD) were unaffected by treatment with GAD65 or β-galactosidase. The background for medium alone ranged from 1300 to 2800 c.p.m. Mice from control and experimental groups were tested simultaneously in two separate experiments (using triplicate cultures). None of the antigens induced significant proliferation of splenic T cells from BALB/c mice (data not shown). Insulitis score was determined as previously described (n = 6 for each group). Kaufman et al., supra.

EXAMPLE 5

GAD65 Treatment Inhibits Disease Progression

Examination of the pancreases from 12-week-old control mice treated with IFA (alone) or β-galactosidase revealed that all islets had infiltrating lymphocytes. The severity of insulitis in control animals (Table 2) was similar to that observed in unmanipulated NOD mice. Kaufman et al., supra. In contrast, in the GAD65-treated group, 40% of the islets were free of lymphocytic infiltrates and insulitis was less severe. Because the treatments were begun well after the onset of insulitis, the presence of some lymphocytic infiltrates in GAD65-treated mice was not unexpected. Thus, administering GAD65 to prediabetic mice inhibited lymphocytic infiltration of the islets.

Approximately 80% of the control mice developed IDDM by 35 weeks of age (FIG. 4), paralleling the disease course observed in unmanipulated female NOD mice. In contrast, 80% of the GAD65-treated mice showed no signs of hyperglycemia at 40 weeks of age (P<0.03). We detected high levels of GAD65 IgG1 autoantibodies in the sera of all 40-week-old GAD65-treated mice that remained disease-free. However, the two GAD65-treated mice that developed IDDM had very low levels of GAD65 autoantibodies at the time of disease onset (data not shown).

Thus, GAD65 administration significantly reduces long-term IDDM incidence. Collectively, the data presented in Examples 1–5 demonstrate that β-cell autoantigen administration, even after the establishment of a pathogenic Th1 response, can induce a protective Th2 response, which shifts the Th1/Th2 balance and is associated with inhibition of disease progression.

EXAMPLE 6

GAD65 Treatment Prolongs Syngeneic Islet Graft Survival

We next examined whether this therapy could be extended to protect transplanted islets from established autoimmune responses in diabetic NOD mice. Immediately following the onset of diabetes, mice were maintained on insulin and were treated with β-galactosidase control antigen, or with one of the following β-cell autoantigens; GAD65, hsp65 (peptide 277), or the B-chain of insulin (which contains the immunodominant determinant; see Muir et al., *J. Clin. Invest.* 95:628–634 (1995) and Daniel et al., *Proc. Natl. Acad. Sci. U.S.A.* 93:956–960 (1996)). Following transplantation of newborn islets, exogenous insulin administration was discontinued and no immunosuppressants were used to block rejection. The results of these experiments are presented in FIG. 5.

As is shown in FIG. 5, we observed that mice treated with the β-galactosidase control antigen, the hsp65 peptide or insulin B-chain became diabetic approximately 10 days post transplantation. In contrast, GAD65-treated mice remained euglycemic for an average of 48 days post transplantation. The GAD65-treated mice had residual islet cell function, which allowed them to survive in a chronic hyperglycemic state up to 20 weeks post transplantation (data not shown).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for prolonging the survival of a pancreatic tissue transplant in a mammal, said method comprising:

administering to said mammal a pancreatic tissue transplant protecting amount of a pancreatic β-cell-associated antigen, wherein said antigen administration results in an increase in the ratio of the number of T helper 2 cells specific for said antigen to the number of T helper 1 cells specific for said antigen.

2. The method according to claim 1, wherein said administering is performed prior to transplantation of said tissue into said mammal.

3. The method according to claim 1, wherein said administering is performed after transplantation of said tissue into said mammal.

4. The method according to claim 1, wherein said pancreatic β-cell-associated antigen is an autoantigen.

5. The method according to claim 4, wherein said pancreatic β-cell-associated autoantigen is GAD65.

6. A method for reducing the severity of an IDDM-associated autoimmune response in a mammal, said method comprising administering to said mammal a therapeutically effective amount of a pancreatic β-cell-associated antigen, wherein said administering results in an increase in the ratio of the number of T helper 2 cells specific for said antigen to the number of T helper 1 cells specific for said antigen.

7. The method according to claim 6, wherein said pancreatic β-cell-associated antigen is selected from the group consisting of GAD65, hsp65 and insulin B-chain.

8. The method according to claim 7, wherein said pancreatic β-cell-associated antigen is GAD65.

9. The method according to claim 6, wherein said pancreatic β-cell-associated antigen is administered in conjunction with an adjuvant.

10. The method according to claim 9, wherein said adjuvant is selected from the group consisting of incomplete Freund's adjuvant, aluminum hydroxide, interleukin-4 and interleukin-10.

11. The method according to claim 6, wherein said administration is parenteral.

12. The method according to claim 11, wherein said parenteral administration is by subcutaneous, intramuscular, intraperitoneal, intracavity, transdermal, or intravenous injection.

13. The method according to claim 6, wherein said administration is at a dosage of about 0.01 mg/kg/dose to about 2000 mg/kg/dose.

14. A method for increasing the frequency of T helper 2 cells specific for a pancreatic β-cell-associated antigen relative to T helper 1 cells specific for said pancreatic β-cell-associated antigen in a mammal comprising administering to said mammal said pancreatic β-cell-associated antigen in an amount sufficient to increase said T helper 2 response relative to said T helper 1 response.

15. The method according to claim 14, wherein said pancreatic β-cell-associated autoantigen is selected from the group consisting of GAD65, hsp65 and insulin B-chain.

16. The method according to claim 14, wherein said pancreatic β-cell-associated autoantigen is GAD65.

17. The method according to claim 14, wherein said pancreatic β-cell-associated antigen is administered in conjunction with an adjuvant.

18. A method for reducing the severity of an ongoing IDDM-associated autoimmune response in a mammal, said method comprising administering to said mammal after the onset of insulitis a therapeutically effective amount of a pancreatic β-cell-associated antigen, wherein administering results in an increase in the ratio of the number of T helper 2 cells specific for said antigen to the number of T helper 1 cells specific for said antigen.

* * * * *